United States Patent
Guidotti

(10) Patent No.: US 6,664,438 B1
(45) Date of Patent: *Dec. 16, 2003

(54) ABSORBENT ARTICLE WITH IMPROVED LIQUID-HANDLING ABILITY

(75) Inventor: Ted Guidotti, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/550,796

(22) Filed: Apr. 17, 2000

(30) Foreign Application Priority Data

May 28, 1999 (SE) .............................................. 9901942

(51) Int. Cl.⁷ ................................................ A61F 13/15
(52) U.S. Cl. .................................. 604/378; 604/385.28
(58) Field of Search ................................ 604/378, 379, 604/380, 385.01, 387, 385.28

(56) References Cited

U.S. PATENT DOCUMENTS

| | | | |
|---|---|---|---|
| 5,308,346 A | * 5/1994 | Sneller et al. ......... | 604/385.25 |
| 5,445,627 A | * 8/1995 | Mizutani et al. ......... | 604/385.2 |
| 5,490,847 A | * 2/1996 | Correa et al. ............. | 604/387 |
| 5,525,407 A | * 6/1996 | Yang ........................ | 428/218 |
| 5,810,800 A | * 9/1998 | Hunter et al. ........... | 604/385.23 |
| 5,885,268 A | * 3/1999 | Bien et al. ............. | 604/385.23 |
| 6,103,953 A | * 8/2000 | Cree et al. .................. | 604/365 |
| 6,159,190 A | * 12/2000 | Tanaka et al. ......... | 604/385.24 |
| 6,198,019 B1 | * 3/2001 | Hansson et al. ............ | 604/378 |
| 6,231,554 B1 | * 5/2001 | Menard ................. | 604/385.01 |
| 6,241,714 B1 | * 6/2001 | Raidel et al. ............... | 604/378 |

\* cited by examiner

Primary Examiner—Weilun Lo
Assistant Examiner—Jamisue A Webb
(74) Attorney, Agent, or Firm—Burns, Doane, Swecker & Mathis, L.L.P.

(57) ABSTRACT

An absorbent article with a longitudinal direction and a transverse direction, a center line (29) running in the longitudinal direction, a center line running in the transverse direction, two side edges (9, 10) running in the longitudinal direction, two end edges (11, 12) running in the transverse direction, and including a liquid-permeable surface layer (2), a liquid-tight surface layer (3), a side barrier pocket (40, 41) arranged along each side edge (9, 10) and having an opening directed towards the longitudinal center line, and an absorption body (4) enclosed between the surface layers (2, 3). The absorption body (4) includes at least one intermediate storage part (22–25) and a liquid transfer part (26). The intermediate storage part (22–25) is arranged along a side edge (9, 10), in direct contact with the liquid transfer part (26), and inside a side barrier pocket (40, 41). The transport of liquid between the material in the intermediate storage part (22–25) and the liquid transfer part (26) is such that the liquid transfer part (26) drains liquid from the intermediate storage part (22–25).

22 Claims, 4 Drawing Sheets

ABSORBENT ARTICLE WITH IMPROVED LIQUID-HANDLING ABILITY

CROSS-REFERENCE TO RELATED APPLICATIONS

The present application corresponds to, and claims the priority of, Swedish Patent Application No. 9901942-4, filed on May 28, 1999, the entire contents of which are incorporated herein by reference.

1. Field of the Invention

The invention relates to an absorbent article with a longitudinal direction and a transverse direction, a center line running in the longitudinal direction, a center line running in the transverse direction, two side edges running in the longitudinal direction, two end edges running in the transverse direction, and comprising a liquid-permeable surface layer, a liquid-tight surface layer, a side barrier pocket arranged along each side edge and having an opening directed towards the longitudinal center line, and an absorption body arranged between the surface layers, the absorption body comprising at least one intermediate storage part and one liquid transfer part.

2. Discussion of Related Art

A common problem associated with an absorbent article such as a diaper or an incontinence pad, which is intended to absorb body fluid, is that fluid leaks out past the side edges of the article. To help prevent side leakage, it is customary to arrange different types of leakage barriers along the side edges of the article. For example, diapers and incontinence pads are often provided with elastic members which, while the article is being used, are tightened around the user's legs and hold the side edges of the article in sealing contact against the legs. Elastic members can also be used to form raised edge barriers. It is also possible to create raised barriers in another way, for example by providing ridges or the like which prevent liquid from flowing freely over the side edges of the article.

However, it has been found that despite all the efforts which have previously been made to avoid leakage at the side edges, the problem still remains, especially in certain applications. When the user is lying in a side position, there is a great risk of side leakage. Body fluid which is excreted in this position tends to run out and gather, by the effect of gravity, at the longitudinal side edge of the article, where the available absorption material quickly becomes oversaturated with liquid. Liquid then remains, which is not absorbed but can run freely along the side edge. The risk is of course great that this liquid will be forced out over the side edge of the article and escape if the user moves in such a way that a gap arises between the article and the user's body.

One reason for the increased risk of leakage when the user is in a side position is that the absorption capacity of the absorbent article has only been utilized to a limited extent. Thus, the absorption material nearest the side edge which is furthest down when the user is lying down is oversaturated, while the main part of the absorption capacity of the article is not used up. It can therefore happen that body fluid leaks out from an article that has unused absorption capacity.

OBJECTS AND SUMMARY

One aim of the present invention is to make available an absorbent article with improved liquid-handling ability. Another aim of the invention is to provide an article with improved safety against leakage, even when the person using the article is lying in a side position. An article according to the invention also has a high degree of utilization of the absorption capacity present in the absorption body of the article. An absorbent article with a longitudinal direction and a transverse direction, a center line running in the longitudinal direction, a center line running in the transverse direction, two side edges running in the longitudinal direction, two end edges running in the transverse direction, and comprising a liquid-permeable surface layer, a liquid-tight surface layer, a side barrier pocket arranged along each of the side edges and having an opening directed towards the longitudinal center line, an absorption body arranged between the surface layers, the absorption body comprising at least one intermediate storage part and a liquid transfer part, the intermediate storage part is arranged along at least one of the side edges, in direct contact with the liquid transfer part, the intermediate storage part is arranged inside the at least one side barrier pocket, and the transport of liquid between material in the intermediate storage part and the liquid transfer part is such that the liquid transfer part drains liquid from the intermediate storage part.

BRIEF DESCRIPTION OF THE DRAWINGS

The invention will be described in greater detail below with reference to the figures which are shown on the attached drawings, and of which.

DETAILED DESCRIPTION OF THE PREFERRED EMBODIMENTS

Figure 1:
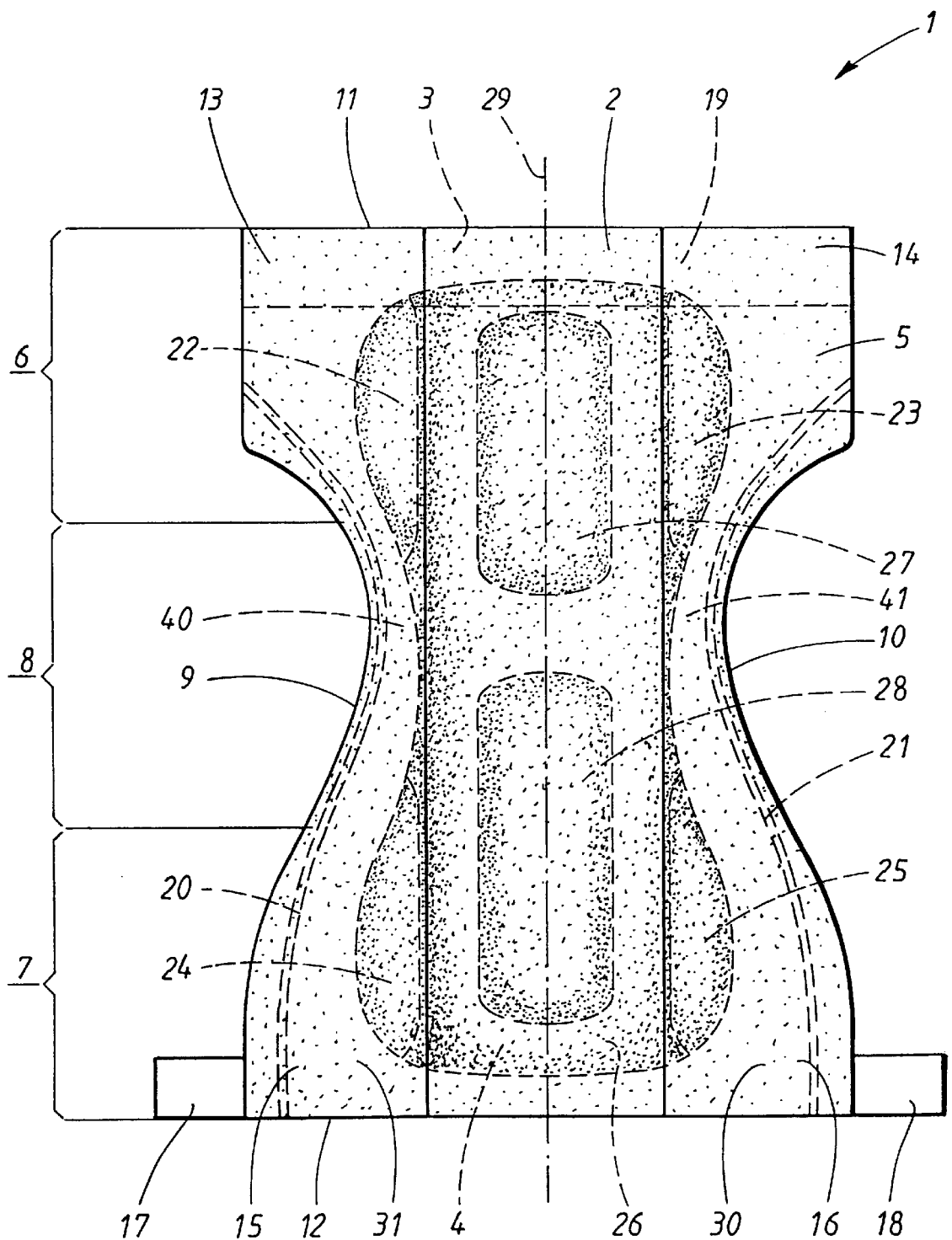
FIG. 1 shows a plan view of a diaper with an absorption body according to the invention.

An absorbent article according to the present invention has an absorption body that includes at least an intermediate storage part and a liquid transfer part. The intermediate storage part is arranged along a side edge of the article, in direct contact with the liquid transfer part, and the intermediate storage part is arranged inside a side barrier pocket. The transport of liquid between the material in the intermediate storage part and the liquid transfer part is such that the liquid transfer part drains liquid from the intermediate storage part.

A purpose of the intermediate storage part arranged in the side barrier pocket is to catch liquid running out to the edge portions of the absorbent article. This generally happens when the person using the article is lying down on his or her side. By choosing the materials of the absorption body in such a way that the liquid transfer part has the ability to drain liquid from the intermediate storage part, liquid which collects in the side barrier pocket can gradually be transported from there by the liquid transfer part. When new liquid reaches the absorbent article, this liquid too can be absorbed by the material in the intermediate storage part. Since the liquid affinity in the intermediate storage part is lower than the liquid affinity in the liquid transfer part, liquid transfer from the intermediate storage part to the liquid transfer part is promoted. The liquid affinity for a certain material compared to another material is dependent on a number of factors familiar to the skilled person, for example capillary pressure, effective pore size, wetting angles, diffusion, the material's ability to chemically bind liquid in a gel, etc.

It is preferable that the absorbent article allows liquid to be transported in a plane and that liquid can pass into and out of the side barrier pockets with as little obstruction as possible. It is therefore preferable that the side barrier pockets are kept open for passage of liquid in the plane even when the user is lying down. It is also preferable, for purposes of obtaining optimum liquid transport in the article, that the different absorbent parts of the absorption body are in direct contact with each other. Because two parts of the absorption body are in direct contact with each other, at least one surface of one of the absorbent parts is bearing against a surface of the other absorbent part, so that liquid can be transferred between the parts without the action of any other component in the absorption body. In addition, there should preferably not be any play or space between the absorbent parts at the contact surfaces, at least when the parts are wet. Such a play or space may interrupt the transport channels in the absorption body, as a result of which the liquid transfer between the absorbent parts may be negatively affected. It is possible, within the scope of the invention, to choose an absorption material which swells when it is wetted. In such a case, the absorbent article can have some play or narrow gaps between adjacent parts before wetting, on condition that the play or gaps is bridged when the structure is wetted and swells. It has proven advantageous to form side barrier pockets by arranging a liquid barrier in the form of a hydrophobic material layer over each intermediate storage area of the absorption body. Such a liquid barrier can be arranged on the inside or on the outside of the liquid-permeable surface layer of the article. As used herein, "inside" of a surface layer is the surface of the surface layer which is directed towards the absorption layer of the article, while the "outside" is that surface which is intended to be directed towards a person wearing the article. The hydrophobic material layer which forms the liquid barrier has a substantial ability to withstand liquid penetration and can, if so desired, be completely liquid-tight. However, it is preferable, above all, that the liquid barrier material has a substantial ability to withstand liquid penetration in that portion which constitutes the actual pocket, i.e., the portion which surrounds the intermediate storage area, while those portions of the liquid barrier material which are situated nearest the pocket opening can be made of a material which is slightly less liquid-tight. Suitable barrier materials are plastic films and hydrophobic, preferably finely porous, nonwoven materials. Layers of wax or similar coatings arranged on the liquid-permeable surface layer can also be used. By arranging the liquid barrier material on the inside of a textile surface layer, the surface layer can take up moisture from the skin, which means that the absorbent article is more comfortable to wear and there is less risk of skin irritation caused by high levels of moisture. To reduce the accumulation of moisture on the surface of the liquid-tight barrier layer, it is also advantageous to use breathable films as the liquid barrier layer.

The hydrophobic material layer can consist of a portion of the liquid-tight surface layer which is folded around the side edge of the article, so that an edge portion of the absorption body of the article, including the intermediate storage part, is thereby enclosed in the liquid-blocking side pocket formed by the folded-around surface layer. Alternatively, the side barrier pocket can be formed by a separate strip of liquid-blocking material which is connected to the liquid-tight surface layer in a substantially liquid-tight seam along the side edge of the article.

The side barrier pockets can be arranged along the entire side edges, or only at one or both of the edge portions of the article.

To ensure that the side barrier pocket is kept open and allows liquid to flow to the intermediate storage part, even when the side barrier pocket is exposed to compression, means for keeping the side barrier pocket open for transfer of liquid to and from the intermediate storage part may be expediently arranged at the opening of the side barrier pocket.

Such means can include, for example, one or more compressed grooves in the absorption body. Another example of a means that can be used for keeping the side pocket open is one or more elastic members attached to the side barrier pocket. It may also be useful to leave the material in the side barrier pocket free from bonds to the absorption material within the pocket, or to leave at least an edge portion of the side barrier pocket free from bonds to the absorption body. It is also possible to attach the side barrier pocket to the absorption material using a binder which dissolves on wetting. The side barrier pockets can be provided with spacing members made of springy cotton, foamed material or similar resilient material. Other means that can be used to prevent the side barrier pocket from closing are materials which expand on wetting. Examples of such materials are viscose-foam, tablets of superabsorbent material, or springy cotton which has been compressed and has been bound in the compressed state with water-soluble binder.

According to a preferred embodiment of the invention, intermediate storage parts can be arranged at both side edges of the article. Intermediate storage parts can also be arranged on both sides of the center line running in the transverse direction of the article.

It is also preferred that the absorption body comprises a storage part which is arranged in direct communication with the liquid transfer part and in direct or indirect communication with the intermediate storage part. The storage part has greater liquid affinity than both the intermediate storage part and the liquid transfer part and has the ability to drain liquid from the liquid transfer part. The storage part is arranged in the article in such a way that liquid is transferred from the intermediate storage part to the storage part via the liquid transfer part. It is advantageous for the storage part to contain material with the ability to bind absorbed liquid. Examples of such materials are the polymers which commonly go by the name of superabsorbents. Superabsorbents are materials which have the capacity to absorb liquid several times the weight of the material itself, forming an aqueous gel.

According to one embodiment of the invention, liquid transfer parts are arranged inside the intermediate storage parts in the transverse direction of the article, between each side edge and the center line running in the longitudinal direction of the article. One or two storage parts are then arranged centrally between the liquid transfer parts along the longitudinal center line. When the article comprises two storage areas arranged along the longitudinal center line, it is expedient for one storage area to be offset towards one end edge of the article, while the other storage area is offset towards the other end edge of the article. In such a design, the absorbent article can be configured with little or no absorption material in the crotch portion. This has several advantages. For example, it is possible to configure the article with a very slender and comfortable crotch portion. In addition, a diaper with such an absorption body can be held in place without requiring elastic members to hold the diaper in contact around the user's legs.

To facilitate the use of the absorption material along the entire length of the article, it is expedient that at least one liquid transfer part runs essentially along the entire longitudinal direction of the article. Correspondingly, a liquid transfer part can be arranged along the entire transverse direction of the article.

The intermediate storage parts are liquid-receiving areas in the absorption body and must therefore be able to rapidly admit liquid and absorb it. The intermediate storage parts also constitute temporary liquid storage spaces and must therefore be able to release liquid relatively easily to a material with greater liquid affinity. One example of a material which has been found to function well in the intermediate storage parts is HTCTMP, i.e., high-temperature chemical thermo-mechanical cellulose pulp, with a bulk of 8 cm$^3$/g. One such suitable cellulose pulp is flash-dried pulp of the type described in WO 94/10957.

The liquid transfer parts should drain liquid from the intermediate storage parts, which means that the material in the liquid transfer parts should preferably be chosen such that it has greater affinity for liquid than does the material in the intermediate storage parts. Suitable materials for the liquid transfer parts are chemical cellulose pulp having a bulk of 6 cm$^3$/g, and materials of the type described in WO 94/10956, with a bulk of between 3 and 3.5 cm$^3$/g.

The absorbed liquid should preferably finally be stored in the storage part, which means that the storage part should have the ability to drain liquid from the liquid transfer parts. This can be achieved using conventional storage materials such as layers of heavily compressed cellulose fibres, cellulose foam, or the like. The storage part may advantageously include superabsorbent material which is able to absorb and bind the absorbed liquid in the form of an aqueous gel. It is also possible to use superabsorbent material alone as the storage material.

The various absorbent parts included in the article can be made of different types of materials with different properties and in particular with differing ability to take up liquid, as has been described above. It is also possible to obtain the desired transport of liquid between the various parts by using an absorbent material which comprises thermoplastic material. Such a material can be bonded by heat so that it has different densities in different areas, as a result of which it is possible, from one and the same starting material, to obtain a material in which liquid is transported in a predetermined manner.

To further increase the safety of the article against leakage, edge barriers can be arranged running in the longitudinal direction along the side edges of the article.

Such edge barriers can include elastic members. It is also possible to form edge barriers by arranging liquid-tight material along the side edges of the article.

For example, the liquid-tight surface layer can have edge portions which run over the side edges of the article. Such edge barriers can be made by folded-back portions of a thin plastic film or can be formed by a stiffer material by casting or pressing. In the latter case, the absorption body of the article can be placed in a cup-shaped, liquid-tight shell, with raised walls all around the periphery of the absorption body.

The liquid-catching side barrier pockets according to the invention can be supplemented with edge barriers or barrier pockets arranged at the front edge of the article and/or its rear edge.

An absorbent article according to the invention can advantageously be fitted on a user by means of securing members, for example a belt or strap, which are attached only centrally on the front or rear edge of the article. The advantage of using securing members of this type is that they prevent the side barrier pockets of the article from being pressed against the body. This facilitates ventilation of the skin in the case of bedridden individuals, at the same time as the central portion of the article catches body fluid which is then conveyed to the side pockets.

Illustrated preferred exemplary examples of the present invention may be found in FIGS. 1–7.

Figure 2:
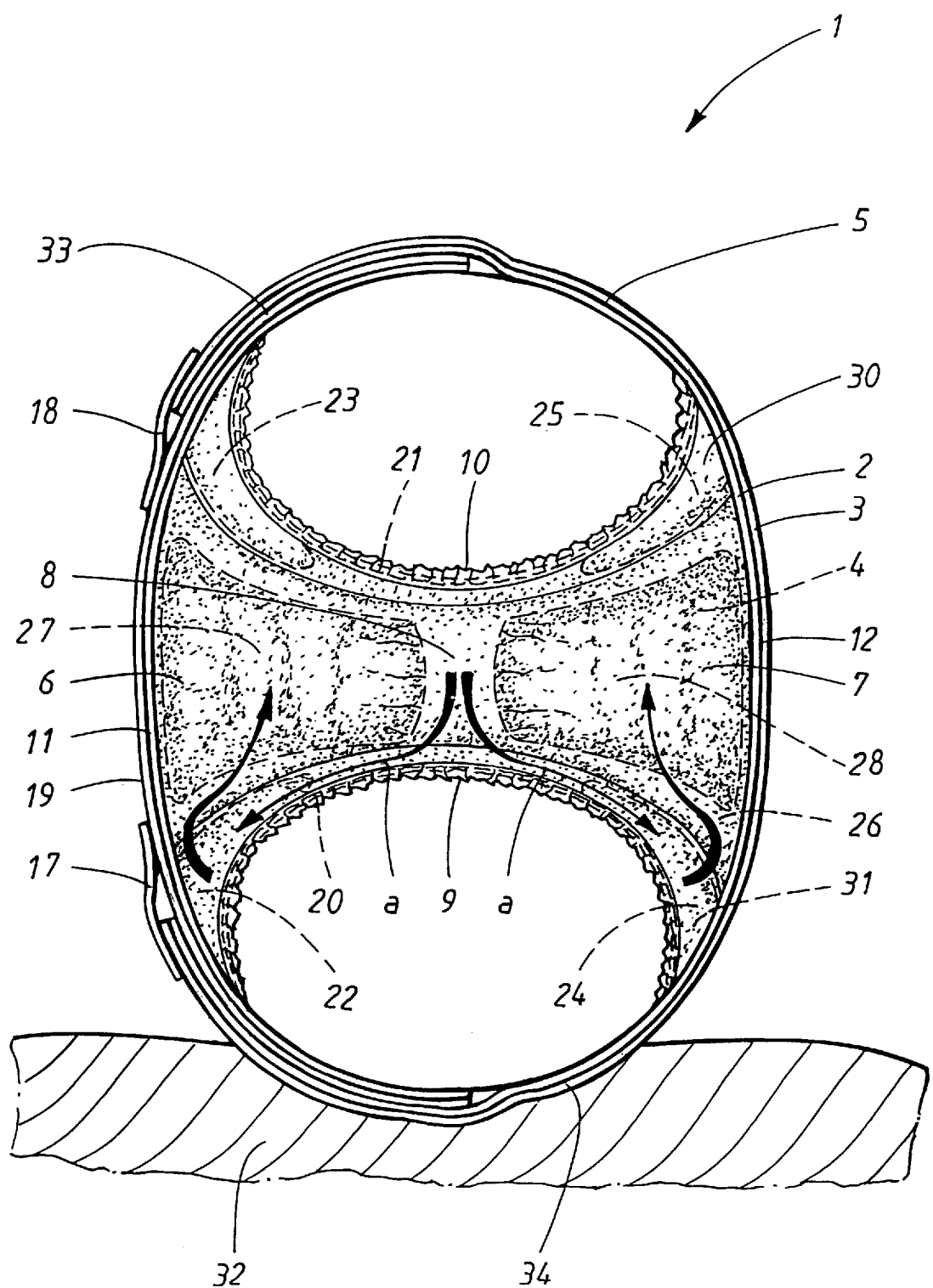
FIG. 2 shows the flow of liquid inside the diaper from FIG. 1 when it is being used.

The diaper 1 shown in FIGS. 1 and 2 comprises a first, liquid-permeable surface layer 2, a second, liquid-tight surface layer 3, and an absorption body 4 arranged between the surface layers 2, 3. The two surface layers 2, 3 have a greater extent in their plane than the absorption body 4 and protrude beyond the absorption body 4 about its entire circumference. The surface layers 2, 3 are connected to each other at the inside of the projecting portions 5, for example, by means of gluing or welding with heat or ultrasound.

The liquid-permeable surface layer 2 can be made of any material known for this purpose, for example, a layer of nonwoven material, perforated plastic film, netting material, or the like. The surface layer 2 can of course also comprise a laminate of two or more layers of the same or different materials. However, the liquid-permeable surface layer 2 does not have to be a separate component, and instead can be an integrated part of the absorption body 4. In such an embodiment, the surface layers 2, 3 do not form a protruding edge 5 around the absorption body 4. Examples of materials which can form the surface layer 2 and can also be included in the absorption body 4 are foam, cotton or the like.

The liquid-tight surface layer 3 can be a liquid-tight plastic film, a nonwoven layer which has been coated with a liquid-blocking material, or some other easily bendable material layer which is able to withstand penetration of liquid. However, it can be advantageous if the liquid-tight surface layer 3 is to some extent able to breathe, i.e., permits passage of water vapour through the layer 3.

The diaper 1 has an elongate shape, with wider front and rear portions 6, 7 and a narrower intermediate crotch portion 8. The front portion 6 is that part of the diaper 1 which is intended to be directed forwards on the user when the diaper is in use, and the rear portion 7 is that part of the diaper which is directed rearwards on the user. The diaper 1 also has two inwardly curved, longitudinal side edges 9, 10, a front edge 11 and a rear edge 12, two front corner portions 13, 14 and two rear corner portions 15, 16.

The diaper 1 is preferably of the type which is held together during use in such a way that, like underwear, it surrounds the lower part of the user's trunk. For this purpose, a tape 17, 18 is arranged projecting from each side edge 9, 10 at the rear edge 12 of the diaper. The tapes 17, 18 are intended to cooperate with a receiving area 19 arranged on the liquid-tight surface layer 3 at the front portion 6 of the diaper 1. Such a receiving area 19 preferably has some form of stiffening, for example, in the form of an extra plastic layer, or a coating applied on the liquid-tight surface layer 3. Of course, it is also possible to imagine using other types of securing arrangements for the diaper 1, such as buttons and buttonholes, hooks and eyelets, press-studs velcro closures, or the like.

The diaper 1 is also provided with prestressed, longitudinal elastic members 20, 21 arranged along the side edges 9, 10 of the diaper. The elastic members 20, 21 are designed to bend the diaper 1 to the shape of the user's body and at the same time they constitute the leg elastic of the diaper. Thus, the elastic members 20, 21 serve to hold the side edges 9, 10 of the diaper in contact against the user's legs, in order to ensure that, during use, little or no play arises between the diaper and the user's body, through which play body fluid could leak from the diaper.

The surface of the absorption body 4 directed towards the liquid-permeable surface layer 2 is divided into different parts which perform different functions in the absorption body. Thus, the absorption body 4 has four intermediate storage parts 22–25 which are arranged at the corner portions 13–16 of the diaper, a liquid transfer part 26 which is arranged nearest the liquid-tight layer 3, as a material layer with the same shape and planar extent as the absorption body 4, and two storage parts 27, 28 arranged along a longitudinal center line 29 through the diaper, at the front portion 6 and rear portion 7, respectively. The materials in the different parts are chosen in such a way that the liquid affinity increases in the direction from the intermediate storage parts 22–25 to the liquid transfer part 26 and onwards to the storage parts 27, 28. In addition, the different parts 22–28 are arranged in relation to each other in such a way that liquid which runs out towards the side edges 9, 10 of the diaper, and is absorbed near the side edges 9, 10, is then actively transported away from the side edges 9, 10 to the storage parts 27, 28.

In order to further increase the safety of the diaper against leakage, barrier strips 30, 31 are arranged along each side edge 9, 10 of the diaper, on the surface which, during use, is intended to be directed towards the user. The barrier strips 30, 31 are shown arranged on the outside of the liquid-permeable surface layer 2, but they can alternatively be arranged on the inside of the liquid-permeable surface layer 2. The barrier strips 30, 31 extend outwards to edge seams 5 on each side edge 9, 10, as a result of which liquid-blocking side pockets 40, 41 are formed at the side edges 9, 10 of the diaper. The barrier strips 30, 31 extend in the transverse direction of the diaper to such an extent that they overlap the intermediate storage areas 22–25.

Suitable liquid-blocking materials for the barrier strips 30, 31 include various types of hydrophobic nonwoven layers, plastic films, or coatings of liquid-resistant material. For reasons of comfort, it is advantageous for the barrier material to be able to breathe, i.e., for it to be permeable to air and vapour. Another way of avoiding accumulation of moisture between the barrier material and the user's body during use is to arrange a thin layer of absorbent material, for example a nonwoven, on the outside of the liquid-blocking side pockets 40, 41.

Material types which are suitable for use in the intermediate storage areas are fiber structures, foam or similar porous material. For example, it is possible to use so-called HTCTMP, which is a cellulose fluff pulp with low wettability.

International patent application PCT/SE98/00078 describes absorbent structures such as fiber structures made of chemi-thermomechanical cellulose fluff pulp (CTMP) in which the surface of the CTMP fibers has been treated with agents for increasing the return wetting angle. With such treatment of CTMP fibers, it has proven possible to increase the return wetting angle from 0°–10° to about 40°, which means that the absorbent structure has relatively low wettability even after wetting.

Other types of absorption material can also be treated to reduce the change in wettability which otherwise often occurs upon wetting.

A dynamic contact angle is to be understood as the angle which is present when a front of liquid is displaced. The terms advance wetting angle and return wetting angle are intended to indicate whether the dynamic contact angle is being measured when a liquid is advancing over a dry surface or when a liquid is retreating over a recently wetted surface.

An agent which can be used to increase the return wetting angle is ethyl hydroxyethyl cellulose (EHEC) which is applied to the absorbent structure, for example by spraying or coating, with a liquid containing the agent, for example, in the form of a solution or suspension, or by any other known method of surface treatment.

If the parts 22–28 included in the absorption body 4 have differences in capillary pressure, it is possible to obtain a controlled and predictable spread of liquid in the absorption body 4.

The material in the liquid transfer part 26 is preferably a material providing good liquid transport. A material which can be used in this connection is chemically produced cellulose fluff pulp (CP) with a grammage of about 200 $g/m^2$. Another material which has been found to function well is the absorption material described in WO 94/10956. This material is a dry-formed fiber layer which is used directly in an absorbent article without first being defibered. Absorbent foam material can also be used as absorption material in the liquid transfer part 26.

The material which is used in the storage parts 27, 28 should have high wettability and capillarity. Suitable materials are mixtures of fluff pulp and highly absorbent polymer materials, commonly called superabsorbents. A superabsorbent material can be present, for example, in the form of fibers, flakes, particles, granules or film and is able to absorb body fluid corresponding to several times its own weight, forming an aqueous gel. Superabsorbents absorb liquid relatively slowly but are able to retain the absorbed liquid, even under pressure. The superabsorbent material can be mixed with cellulose fibers, for example. Alternatively, the superabsorbent material can be arranged between layers of material providing good liquid transport, such as layers of tissue material, or the like. An advantage of such an arrangement is that liquid quickly reaches the greater part of the superabsorbent material.

FIG. 2 illustrates how body fluid spreads inside the diaper 1, shown in FIG. 1, when the user is lying in a side position. In the figure, the user's body has been omitted and the diaper is viewed from the opening at the user's waist, in the direction towards the crotch portion 8. In the figure, the diaper is directed with the front portion 6 towards the left of the figure, while the rear portion 7 is directed towards the right. The user is also lying on a support 32, so that the diaper has an upper part 33 and a lower part 34 which is resting on the support 32.

When urine is passed, liquid is mainly excreted in the crotch portion 8 of the diaper, between the two storage areas 27, 28. Since the user is lying down, some of the liquid will run down, under the effect of gravity, to the lower part 34 of the diaper, as is indicated by the arrows a. Much of the liquid will run down to the intermediate storage parts 22, 24 situated in the lower part 34, which parts 22, 24 are those parts of the diaper which are located the furthest down, nearest the support 32. The body fluid is absorbed in the intermediate storage parts 22, 24 and is thereby prevented from running out over the lower side edge 9 of the diaper. The liquid accumulated in the intermediate storage parts 22, 24 is gradually taken up by the material in the liquid transfer part 26 bordering the intermediate storage parts 22, 24, since the material in this part 26 has greater liquid affinity than the material in the intermediate storage parts 22, 24. The liquid is then carried onwards from the liquid transfer part 26 to the storage parts 27, 28, where it finally remains. The transport of liquid between the liquid transfer part 26 and the storage parts 27, 28 is also actively achieved as an effect of the difference in liquid affinity between these areas.

Figure 3:
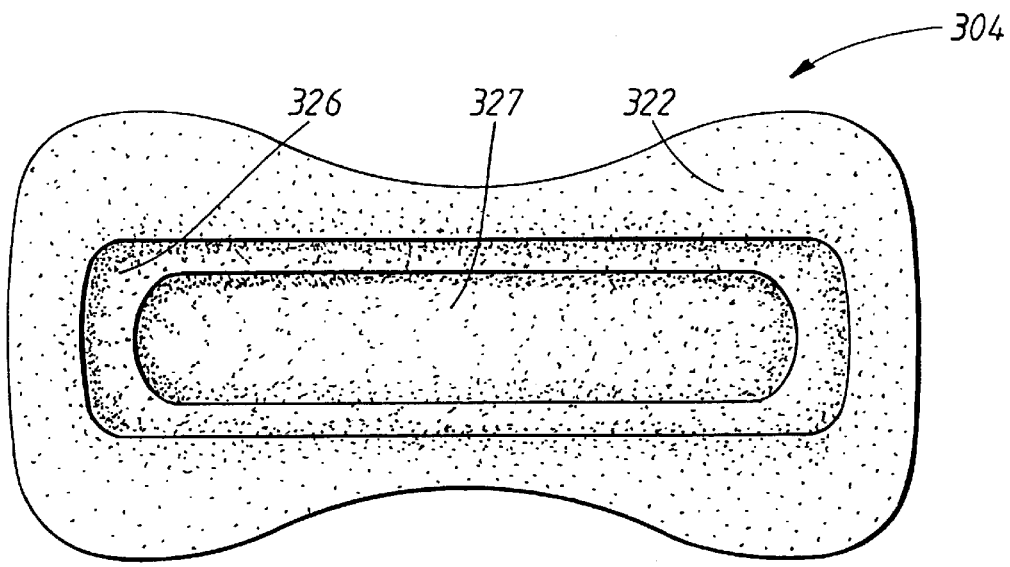
FIG. 3 shows a first alternative embodiment of an absorption body according to the invention.

FIG. 3 shows an alternative absorption body 304 with a single central, longitudinal storage part 327 which, in the plane of the absorption body 304, is surrounded by a liquid transfer part 326, which is in turn surrounded by an intermediate storage part 322. The various parts can comprise layers of material stacked one upon the other, the liquid transfer part 326 having a greater planar extent than the storage part 327, and the intermediate storage part 322 having a greater planar extent than the liquid transfer part 326. In such an embodiment, the intermediate storage part 322 is preferably arranged nearest the surface which is intended to be directed towards a user when the absorption body 304 is arranged in an absorbent article. However, it is preferable that there are, in the transverse direction of the absorption body, portions of the intermediate storage part 322 which are arranged outside the liquid transfer part 326 and that the liquid transfer part 326 correspondingly has portions which, viewed in the transverse direction of the absorption body 304, are arranged outside the storage part 322.

Figure 4:
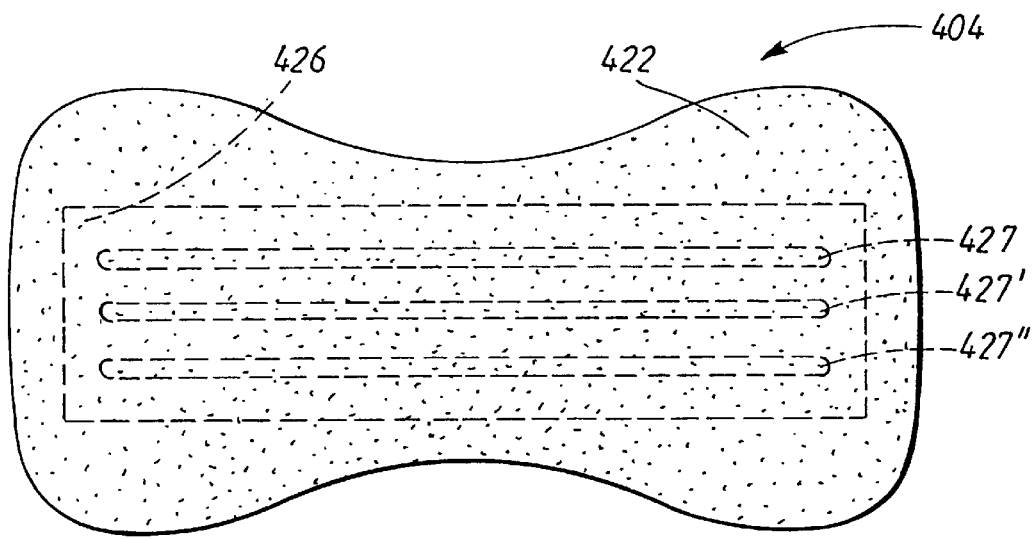
FIG. 4 shows a second alternative embodiment of an absorption body according to the invention.

FIG. 4 shows another embodiment of an absorption body 404 with a continuous intermediate storage part 422 which is arranged about a central, rectangular liquid transfer part 426. In this figure, the absorption body 404 is viewed from the surface which, during use of the absorption body in an absorbent article, is intended to be directed towards the person using the article. The intermediate storage part 422 is formed by a continuous liquid-receiving layer which is arranged over the liquid transfer part 426. Between the liquid transfer part 426 and the intermediate storage part 422, or below the liquid transfer part 426, i.e., furthest away from a person studying FIG. 4, there are three strips of liquid-storing material which constitute liquid storage parts 427, 427', 427".

Figure 5:
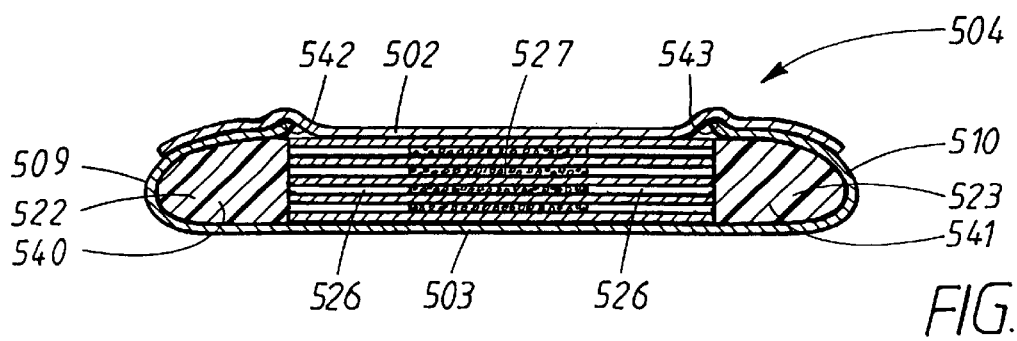
FIG. 5 shows a third alternative embodiment of an absorption body according to the invention.

FIG. 5 shows, in cross section, another embodiment with a centrally arranged storage part 527 consisting of layers of liquid-spreading material, with superabsorbent material arranged between the layers of liquid-spreading material. The superabsorbent material is only arranged in a central portion of the laminate. Thus, the liquid-spreading material extends in the transverse direction past the superabsorbent material on both sides of the storage part 527 and forms liquid transfer parts 526 which are in direct communication with intermediate storage parts 522, 523 arranged at the side edges 509, 510 of the article.

The absorbent article 504 shown in FIG. 5 also has side barrier pockets 540, 541 which are formed by means of the liquid-tight surface layer 503 being folded back around the intermediate storage parts 522, 523 at the side edges 509, 510 of the article. The folded-back portions of the liquid-tight surface layer 503 thus form side barrier pockets 540, 541 which are open towards the liquid transfer parts 526 and allow liquid excreted by the user to pass in to the intermediate storage parts 522, 523 and thereafter be transported to the storage part 527 via the liquid transfer parts 526. To ensure that liquid excreted runs into the side barrier pockets 540, 541, an edge flap 542, 543 is arranged on each side barrier pocket 540, 541, free from attachments to the absorption body 504. A gap is thereby formed between each edge flap 542, 543 and the absorption body 504 in which liquid can be slowed down and guided into the side barrier pocket 540, 541.

The effect of the free edge flaps 542, 543 can be further increased by arranging elastic members in each edge flap 542, 543. Such elastic members help to lift the edge flap up from the surface of the absorption body 504 and to form an edge which slows down the flow of liquid and guides the latter into the side pocket 540, 541.

Although it is preferable, for reasons of comfort, to arrange the liquid-permeable surface layer 502 outside of a liquid-tight surface layer 503 of plastic film, it is of course possible instead to arrange the liquid-tight surface layer 503 on the outside. An advantage of such an embodiment is that the slowing effect of a raised edge flap 542, 543 is greater than when the edge flap is covered by the liquid-permeable surface layer 502.

Figure 6:
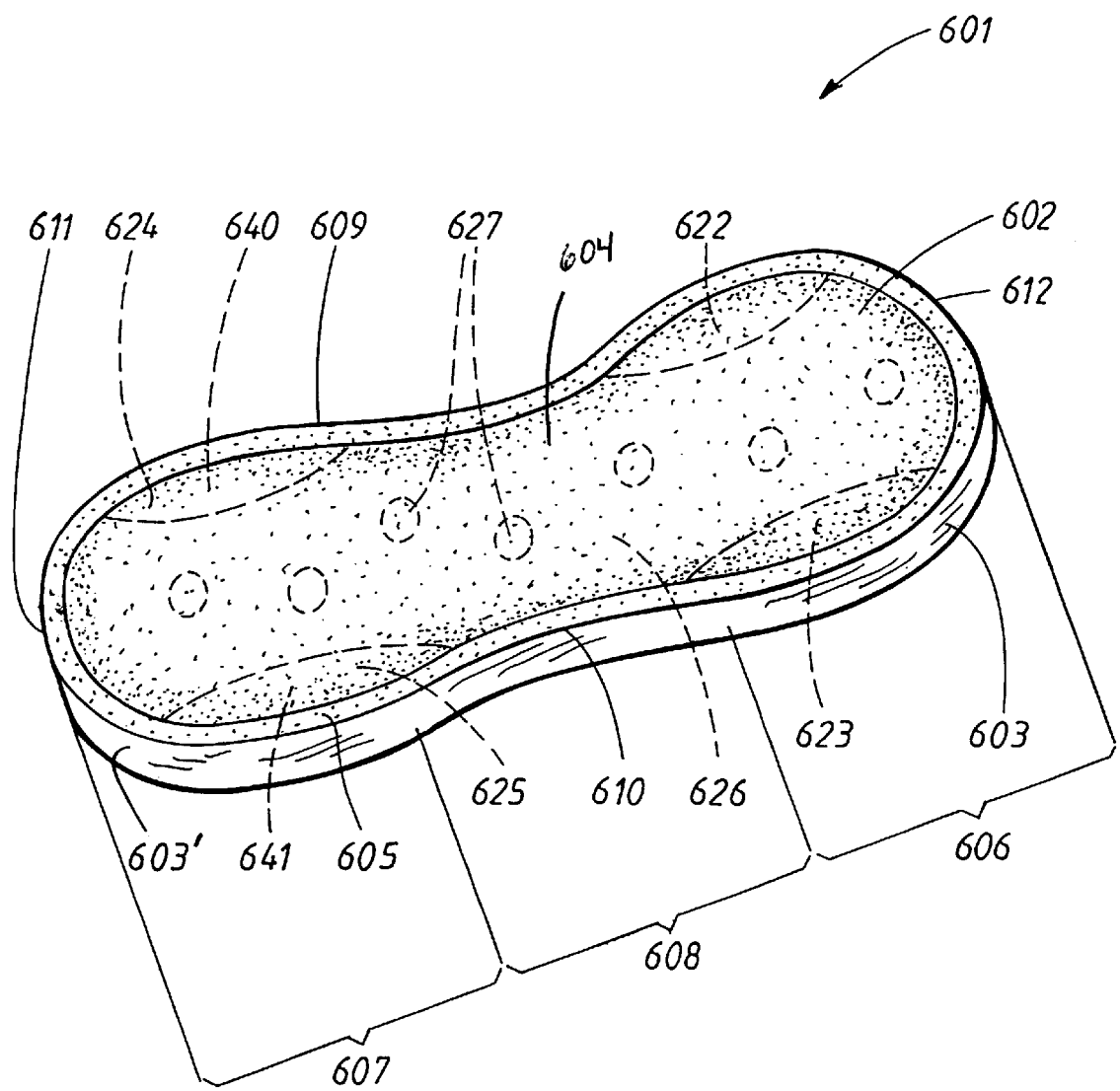
FIG. 6 shows an incontinence pad according to the invention.

FIG. 6 shows an incontinence pad 601 which is of the type intended for individuals with mild incontinence. Such an incontinence pad has a size which allows the incontinence pad to be fitted in the crotch area of normal underwear.

The incontinence pad 601 is provided with a liquid-tight surface layer 603 which is formed into a cup-shaped container for the absorption body 604 of the incontinence pad 601. A liquid-permeable surface layer 602 is arranged over the absorption body 604 and is secured to the liquid-tight surface layer 603 in a continuous edge seam 605.

The cup-shaped container which is formed by the liquid-tight surface layer 603 has an edge wall 603' which extends along the side edges 609, 610 and end edges 611, 612 of the article. The edge wall 603' has a height which corresponds to the thickness of the absorption body 604, as a result of which the edges of the absorption body 604 are covered by liquid-tight material. The edge wall 603' forms, together with the liquid-tight surface layer 603, side barrier pockets 640, 641 which prevent liquid, accumulated in the intermediate storage parts 622–625, from running out of the incontinence pad.

A cup-shaped, liquid-tight surface layer can be made, for example, of a foamed material layer, a plastic layer, or cardboard material which has been coated with liquid-tight material.

The cup shape can also be obtained by using elastic members.

The absorption body 604 can be structured as shown in any of FIGS. 1 to 5, or, as is shown in FIG. 6, it can be structured with intermediate storage parts 622–625 arranged in each end portion 606, 607 of the article, along the longitudinal side edges 609, 610, with a liquid transfer part 626 arranged inside of the intermediate storage parts 622–625 in the transverse direction, and with a number of small circular storage parts 627 distributed across the surface of the liquid transfer area 626.

Figure 7:
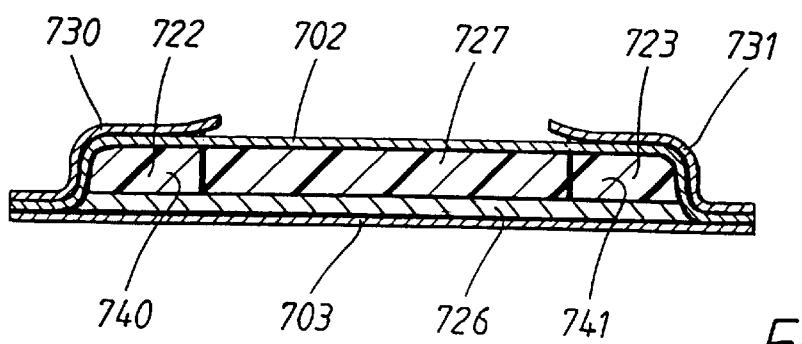
FIG. 7 shows a cross section through an absorbent article according to a further embodiment of the invention.

FIG. 7 shows a cross section through an absorbent article in which the liquid transfer part 726 extends as a continuous layer across the whole width of the article, inside the liquid-tight surface layer 703. The intermediate storage parts 722 and 723 are thus both directly and indirectly in contact with the liquid storage part 727 via the liquid transfer part 726.

Liquid-blocking side barrier pockets 740, 741 are formed by means of liquid-tight barrier strips 730, 731 being arranged on the outside of the liquid-permeable surface layer so that the intermediate storage parts are situated inside the side barrier pockets 740, 741.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article with a longitudinal direction and a transverse direction, a center line running in the longitudinal direction, a center line running in the transverse direction, two side edges running in the longitudinal direction, and two end edges running in the transverse direction, the absorbent article comprising:

a liquid-permeable surface layer, a liquid-tight surface layer, a side barrier pocket arranged along each of the side edges and having an opening directed towards the longitudinal center line, an absorption body arranged between the surface layers, the absorption body comprising at least one intermediate storage part and a liquid transfer part, the intermediate storage part comprising at least two opposite parts separated from each other by other portions of the absorption body and arranged at each of the side edges, at least one of the opposite parts of the intermediate storage part being in direct contact with the liquid transfer part and at least one of the opposite parts being arranged at least partially inside one of the side barrier pockets, and the transport of liquid between material in the intermediate storage part and the liquid transfer part is such that the liquid transfer part drains liquid from the intermediate storage part.

2. The absorbent article according to claim 1, wherein the article has an end portion at each end edge, and a crotch portion situated between the end portions, and the side barrier pockets are arranged along the side edges on at least one end portion.

3. The absorbent article according to claim 1, wherein the side barrier pocket is formed by arranging a liquid barrier in the form of a hydrophobic material layer over the intermediate storage part next to the liquid-permeable surface layer.

4. The absorbent article according to claim 1, wherein the side barrier pockets are formed by the liquid-tight surface layer having edge portions which are folded around side edges of the article.

5. The absorbent article according to claim 1, wherein means for facilitating liquid transfer to and from the intermediate storage part is arranged next to openings of the side barrier pocket.

6. The absorbent article according to claim 5, wherein the means for facilitating liquid transfer to and from the intermediate storage part comprises one or more compressed grooves in the absorption body.

7. The absorbent article according to claim 5, wherein the means for facilitating liquid transfer to and from the intermediate storage part comprises an edge portion of the side barrier pocket, which edge portion is free from bonds to the absorption body.

8. The absorbent article according to claim 5, wherein the means for facilitating liquid transfer to and from the intermediate storage part comprises an elastic member attached to the side barrier pocket.

9. The absorbent article according to claim 5, wherein the means for facilitating liquid transfer to and from the intermediate storage part comprises a spacing member.

10. The absorbent article according to claim 1, wherein a portion of the liquid-tight surface layer forms the side barrier pocket and is arranged between the liquid-permeable surface layer and the intermediate storage layer.

11. The absorbent article according to claim 1, wherein the absorption body further comprises a storage part which is arranged in direct communication with the liquid transfer part and in direct or indirect communication with the intermediate storage part.

12. The absorbent article according to claim 1, wherein said opposite parts of the intermediate storage part are arranged on both sides of the center line running in the transverse direction of the article.

13. The absorbent article according to claim 11, wherein the absorption body further comprises a storage part which is arranged in direct communication with the liquid transfer part and in direct or indirect communication with the intermediate storage part.

14. The absorbent article according to claim 13, wherein liquid transfer parts are arranged inside the intermediate storage parts, between each side edge and the center line running in the longitudinal direction of the article, and also the storage part is arranged centrally between the liquid transfer parts.

15. The absorbent article according to claim 14, wherein the absorption body has two storage parts arranged along the longitudinal center line.

16. The absorbent article according to claim 1, wherein at least one liquid transfer part runs essentially along the entire longitudinal direction of the article.

17. The absorbent article according to claim 1, wherein at least one liquid transfer part runs essentially along the entire transverse direction of the article.

18. The absorbent article of claim 1, wherein a liquid affinity of the liquid transfer part is higher than a liquid affinity of the intermediate storage part so that the liquid transfer part drains liquid from the intermediate storage part better than the intermediate storage part drains liquid from the liquid transfer part.

19. The absorbent article according to claim 1, wherein liquid can pass into and out of the side barrier pockets with as little obstruction as possible.

20. The absorbent article according to claim 1, wherein each of the opposite parts are in direct contact with the liquid transfer part and each of the opposite parts is arranged at least partially inside one of the side barrier pockets.

21. The absorbent article according to claim 1, wherein a liquid affinity of the liquid transfer part is higher than liquid affinities of the opposite parts, and wherein the liquid transfer part drains liquid from at least one of the opposite parts of the intermediate storage part.

22. The absorbent article according to claim 1, wherein a liquid affinity of the liquid transfer part is higher than a liquid affinity of the opposite parts, and wherein the liquid transfer part drains liquid from a lower of the opposite parts when a wearer is lying on a side.

* * * * *